United States Patent
Danz et al.

(10) Patent No.: US 11,413,382 B2
(45) Date of Patent: Aug. 16, 2022

(54) CIRCUIT FOR CONNECTING A PROTECTIVE CONDUCTOR TO AT LEAST TWO LIQUID-CONVEYING LINES AND METHOD FOR CHECKING A PROTECTIVE CONDUCTOR CONNECTION

(71) Applicant: FRESENIUS MEDICAL CARE DEUTSCHLAND GMBH, Bad Homburg (DE)

(72) Inventors: Tim Danz, Schweinfurt (DE); Thomas Schmitt, Dittelbrunn (DE); Berthold Breitkopf, Schweinfurt (DE); Paul Aschenbrenner, Schonungen (DE); Oswald Scheuring, Uchtelhausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 218 days.

(21) Appl. No.: 16/755,888

(22) PCT Filed: Oct. 15, 2018

(86) PCT No.: PCT/EP2018/078076
§ 371 (c)(1),
(2) Date: Apr. 14, 2020

(87) PCT Pub. No.: WO2019/076814
PCT Pub. Date: Apr. 25, 2019

(65) Prior Publication Data
US 2021/0196877 A1    Jul. 1, 2021

(30) Foreign Application Priority Data
Oct. 19, 2017   (DE) ..................... 10 2017 009 752.6

(51) Int. Cl.
*A61M 1/16*    (2006.01)

(52) U.S. Cl.
CPC ....... *A61M 1/1621* (2014.02); *A61M 2205/16* (2013.01); *A61M 2205/70* (2013.01)

(58) Field of Classification Search
CPC .... A61M 1/14; A61M 1/1621; A61M 1/1656; A61M 1/367; A61M 2205/16; A61M 2205/70
See application file for complete search history.

(56) References Cited

U.S. PATENT DOCUMENTS

2009/0210162 A1    8/2009   Kristiansen et al.

FOREIGN PATENT DOCUMENTS

| EP | 0846470 A1 | 6/1998 |
|---|---|---|
| EP | 1623733 A2 | 2/2006 |
| WO | 2004108206 A1 | 12/2004 |

OTHER PUBLICATIONS

International Preliminary Report on Patentability issued in corresponding International Patent Application No. PCT/EP2018/078076 (English translation) dated Apr. 21, 2020 (5 pages).
(Continued)

*Primary Examiner* — Dirk R Bass
(74) *Attorney, Agent, or Firm* — Kilyk & Bowersox, P.L.L.C.

(57) ABSTRACT

The invention relates to a circuit arrangement for a protective-conductor connection to at least two fluid-conducting lines 11, 12, in particular to at least two fluid-conducting lines which are guided outwards from the interior of a housing 1 of a medico-technical device, in particular the housing of a blood treatment device. The circuit arrangement comprises a plurality of protection apparatuses 16A, 16B; 17A, 17B for electrical contacting which are designed such that an electrical connection to a fluid in the line can be produced using each protection apparatus for electrical contacting. In the circuit arrangement, at least two protection apparatuses 16A, 16B; 17A, 17B for electrical contacting (Continued)

Figure 1:
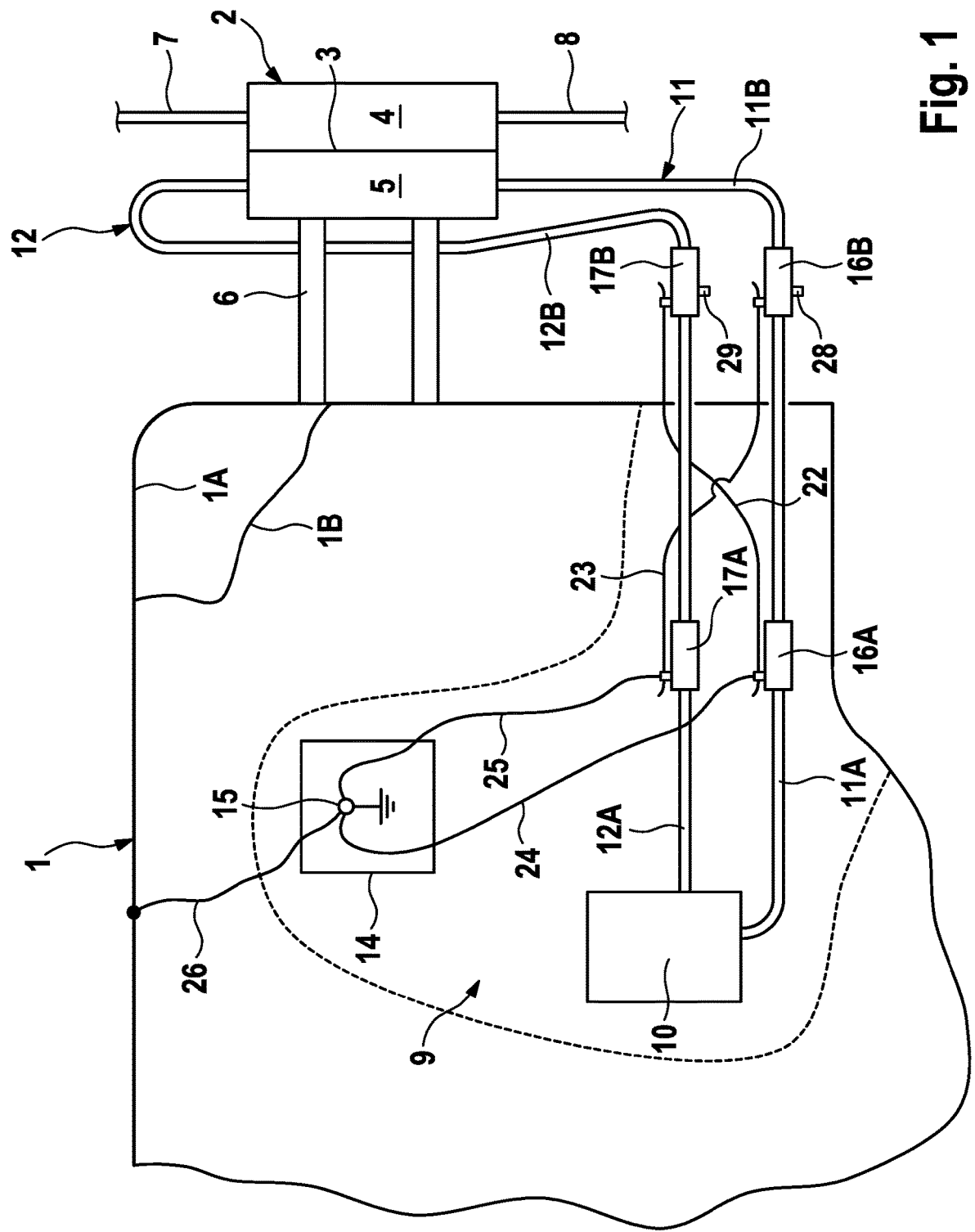

are assigned to each fluid-conducting line 11, 12. As a result, two protective measures are taken for each fluid-conducting line. In addition, the protection apparatuses 16A, 16B; 17A, 17B of one fluid-conducting line 11; 12 are each electrically connected to another protection apparatus 16A, 16B; 17A, 17B of another fluid-conducting line 11; 12. The protective-conductor concept according to the invention improves safety for the patient and makes it possible to test the protective-conductor connection in a simple manner.

19 Claims, 4 Drawing Sheets

(56) References Cited

OTHER PUBLICATIONS

International Search Report and Written Opinion issued in corresponding International Patent Application No. PCT/EP2018/078076 (with English translation of International Search Report) dated Jan. 21, 2019 (7 pages).

CIRCUIT FOR CONNECTING A PROTECTIVE CONDUCTOR TO AT LEAST TWO LIQUID-CONVEYING LINES AND METHOD FOR CHECKING A PROTECTIVE CONDUCTOR CONNECTION

This application is a National Stage Application of PCT/EP2018/078076, filed Oct. 15, 2018, which claims priority to German Patent Application No. 10 2017 009 752.6, filed Oct. 19, 2017.

The invention relates to a circuit arrangement for a protective-conductor connection to at least two fluid-conducting lines, in particular to at least two fluid-conducting lines which are guided outwards from the interior of a housing of a medico-technical device, in particular the housing of a blood treatment device. The invention further relates to a medico-technical device comprising a housing and at least two fluid-conducting lines and a circuit arrangement of this kind, and to a method for testing the protective-conductor connection to at least two fluid-conducting lines which are guided outwards from the interior of a housing of a medico-technical device, in particular the housing of a blood treatment device.

Medico-technical devices, in particular blood treatment devices, require particular electrical protective measures in order to meet electrical safety requirements. For the power supply, the medico-technical devices have a power unit comprising a central protective-conductor connection that is connected to the protective-conductor system of the fixed electrical installation, which system is at earth potential. The safety check (SC) of medico-technical devices involves testing the electrical resistance of the protective-conductor connection.

For dialysis devices, a protective measure for meeting the electrical safety requirements (IEC 60601-1) is attaching an electrical protection apparatus to the fluid-conducting lines of the fluid part, in order to produce an electrical connection to the fluids located in the fluid lines. Said protection apparatus can be in the form of a tubular body made of an electrically conductive material, to which body the fluid line is connected. The tubular body, which is also referred to as a bush, is connected to a protective conductor or an equipotential bonding system via a connecting line. The bush can also be inserted into a recess in the housing, in order to guide a fluid line out of the housing. In the known dialysis devices, only a single protection apparatus for contacting of this kind is assigned to a fluid line.

The known blood treatment devices, in particular dialysis devices, have an extracorporeal blood circuit and a dialysate part or dialysate circuit. The extracorporeal blood circuit includes the blood chamber of a dialyser (filter), and the dialysate part includes the dialysate chamber of a dialyser, which is divided into the two chambers by a semi-permeable membrane. The dialyser is generally an exchangeable unit, which is attached to the outside of the housing of the dialysis device so as to be easily accessible.

The dialysis devices may have an apparatus for producing dialysate from fresh water and concentrates that is within the housing. The fresh dialysate is supplied to the dialysate chamber from the apparatus for producing dialysate via a dialysate supply line, and used dialysate is removed from the dialysate chamber via a dialysate return line. Since the dialyser is not in the housing of the dialysis device, the dialysate lines have to be guided outwards from the interior of the housing.

The object of the invention is to provide an improved protective-conductor concept. In particular, the object of the invention is to provide a circuit arrangement by means of which the electrical safety of medico-technical devices, in particular dialysis devices, can be improved in a relatively simple technical manner. An additional object of the invention is to provide a medico-technical device that has an improved protective-conductor connection. Another object of the invention is to simplify the testing of the protective-conductor connection, and to provide a method that allows the protective-conductor connection to be tested in a simple manner using the circuit arrangement according to the invention.

These objects are achieved according to the invention by the features of the independent claims. The dependent claims relate to advantageous embodiments of the invention.

The circuit arrangement according to the invention comprises a plurality of protection apparatuses for electrical contacting which are designed such that an electrical connection to a fluid in the line can be produced using each protection apparatus for electrical contacting. Such protection apparatuses for electrical contacting can be, for example, in the form of tubular bodies, to the end pieces of which the fluid-conducting lines can be connected. The end pieces may be designed as terminal pieces to which hose lines can be attached. For example, the hose lines can be easily slid onto the end pieces. It is, however, possible for the end pieces to have plugs or sockets, or other connectors. The protection apparatuses may be designed as housing feedthroughs. The electrical connection to the fluid in the fluid line can be produced by the protection apparatuses consisting of an electrically conductive material, in particular metal. However, the protection apparatuses may also consist of an electrically non-conductive material if they have electrically conductive inserts, in particular metal pieces, in contact with the fluid.

The circuit arrangement according to the invention is characterised in that at least two protection apparatuses for electrical contacting are assigned to each fluid-conducting line. As a result, two protective measures (MOP: means of protection) are taken for each fluid-conducting line. As a result, the electrical safety is improved without other measures, for example additional design measures for increasing air gaps or leakage paths and/or for improved electrical insulation being required. Safety for a patient connected to the fluid-conducting lines is increased overall since the lines are connected, in two separate measures, to a protective conductor or a protective potential.

The circuit arrangement according to the invention is further characterised in that the at least two protection apparatuses for electrically contacting a fluid-conducting line are each electrically connected to another protection apparatus for electrically contacting another fluid-conducting line. As a result, one of the at least two protection apparatuses for electrical contacting assigned to one of the fluid-conducting lines is electrically connected to one of the at least two protection apparatuses for electrical contacting assigned to the other fluid-conducting line, while another of the at least two protection apparatuses for electrical contacting assigned to one of the fluid-conducting lines is electrically connected to another of the at least two protection apparatuses for electrical contacting assigned to the other fluid-conducting line.

The advantage of the electrical connection of the protection apparatuses assigned to the two fluid-conducting lines is that upon failure of the protective-conductor connection of one fluid-conducting line, for example as a result of a conductor interruption, said line is still connected to the protective conductor or equipotential bonding system by means of the protective-conductor connection of the other fluid-conducting line. The increase in redundancy leads to increased safety for the patients.

Additional advantages of the circuit arrangement according to the invention come into effect when the fluid lines are guided outwards from inside the housing, i.e. penetrate the housing wall. This means that, out of the at least two protection apparatuses for electrical contacting assigned to each fluid-conducting line, at least one protection apparatus for electrical contacting is assigned to a line portion of the fluid-conducting line that is inside the housing, and at least one protection apparatus for electrical contacting is assigned to a line portion of the fluid-conducting line that is outside the housing, at least in part. In a preferred embodiment, a protection apparatus for electrically contacting a fluid-conducting line that is assigned to the line portion of one of the fluid-conducting lines that is inside the housing is electrically connected to a protection apparatus for electrically contacting another fluid-conducting line that is assigned to the line portion of the other fluid-conducting line that is outside the housing, at least in part. The protection apparatuses assigned to the line portion of the fluid-conducting line that is inside the housing are each connected to a protective conductor or an equipotential bonding system by means of an electrical connecting line.

If some of the protection apparatus is inside the housing and some of the protection apparatus is outside the housing, a line portion is located outside the housing, at least in part, relative to the position of the protection apparatus assigned thereto. This is the case in particular if the protection apparatus is mounted in the housing wall as a housing feedthrough and the protection apparatus is preferably electrically contacted at the part of the protection apparatus facing inside the housing. In this embodiment, cable connections that penetrate the housing are avoided. A protection apparatus designed as a housing feedthrough can be mounted so as to be electrically insulated with respect to the housing, for example by means of circumferential insulators.

This protective-conductor concept having a "crosswise" connection of the protection apparatuses makes it possible to test all of the protective-conductor connections of a fluid-conducting line in an especially simple manner using only resistance measurements, which can be carried out without opening the housing since two separate measurement points are provided on the protection apparatuses, which apparatuses are accessible from the outside and are assigned to the line portion of the fluid-conducting line that is outside the housing. In addition, earthing of the lines is also then ensured by means of said protective-conductor concept if one of the electrical connecting lines at the protective conductor or equipotential bonding system is intended to be interrupted. The earthing is then carried out via the other connecting line. It can thus be determined by means of one measurement whether all the fluid-conducting lines are connected to the protective conductor via at least one protection apparatus.

The method according to the invention for testing a protective-conductor connection to at least two fluid-conducting lines that are guided outwards from the interior of a housing of a medico-technical device by means of the circuit arrangement according to the invention measures the electrical resistance between the protection apparatuses for electrical contacting that are assigned to the line portions of the fluid-conducting lines that are outside the housing and the protective conductor or equipotential bonding system.

In one embodiment, the housing of the medico-technical device consists of an electrically conductive material, the protective conductor or equipotential bonding system being electrically connected to the housing. If the protective conductor or equipotential bonding system is electrically connected to an electrically conductive housing, the electrical resistance between the outer protection apparatuses for electrical contacting and the housing can be measured in a simple manner, without needing to open the housing, since all of the measurement points are accessible from the outside.

In an alternative embodiment, a housing of the medico-technical device consists of an electrically non-conductive material, the protective conductor or equipotential bonding system being electrically connected to an electrical measurement contact point on the electrically non-conductive housing, which contact point is accessible from the outside. In this embodiment, the electrical resistance between the outer protection apparatuses and the measurement contact point can be measured in a simple manner. Alternatively or additionally, the electrical resistance between the outer protection apparatuses and the protective-earth contact in the mains plug of the medico-technical device can be measured.

The protective conductor or equipotential bonding system can be connected to the protective-conductor system of a fixed electrical installation.

The at least two fluid-conducting lines can be part of a fluid system of the medico-technical device which is also referred to as a hydraulic system. A medical fluid, in particular dialysate, can be located in the fluid-conducting lines. The medico-technical device can comprise a first fluid-conducting line and a second fluid-conducting line, the two fluid-conducting lines forming a fluid circuit which can include a supply line and a return line. The fluid circuit can be produced by the ends of the fluid line being interconnected. The connection can take place by means of a short-circuit part or a dialyser (filter). In a dialysis device, the fluid system can include the dialysate supply line leading to the dialyser (filter) and the dialysate return line leading away from the dialyser (filter).

Figure 2:
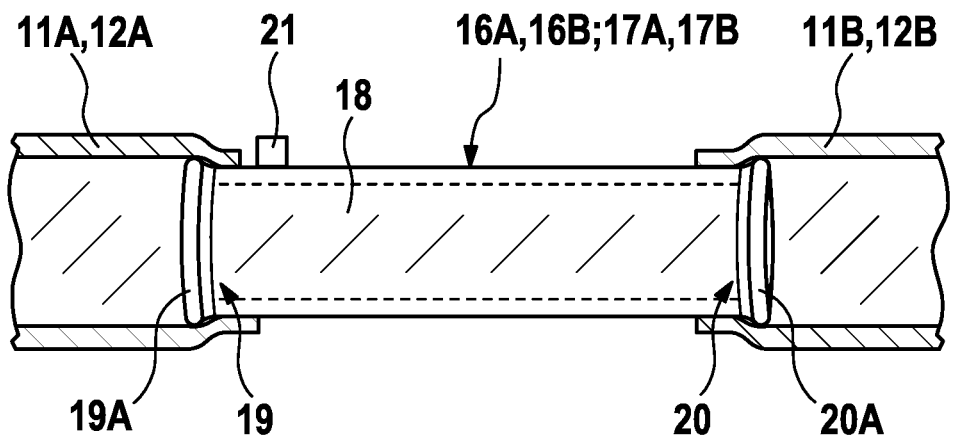
Figure 3:
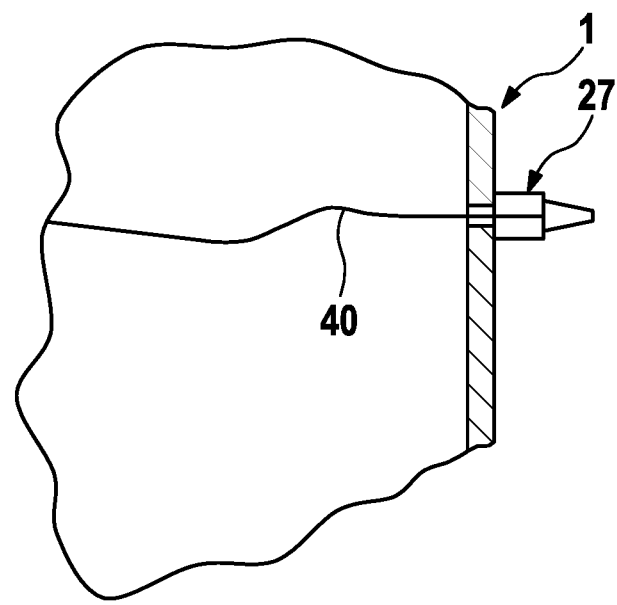
Figure 4:
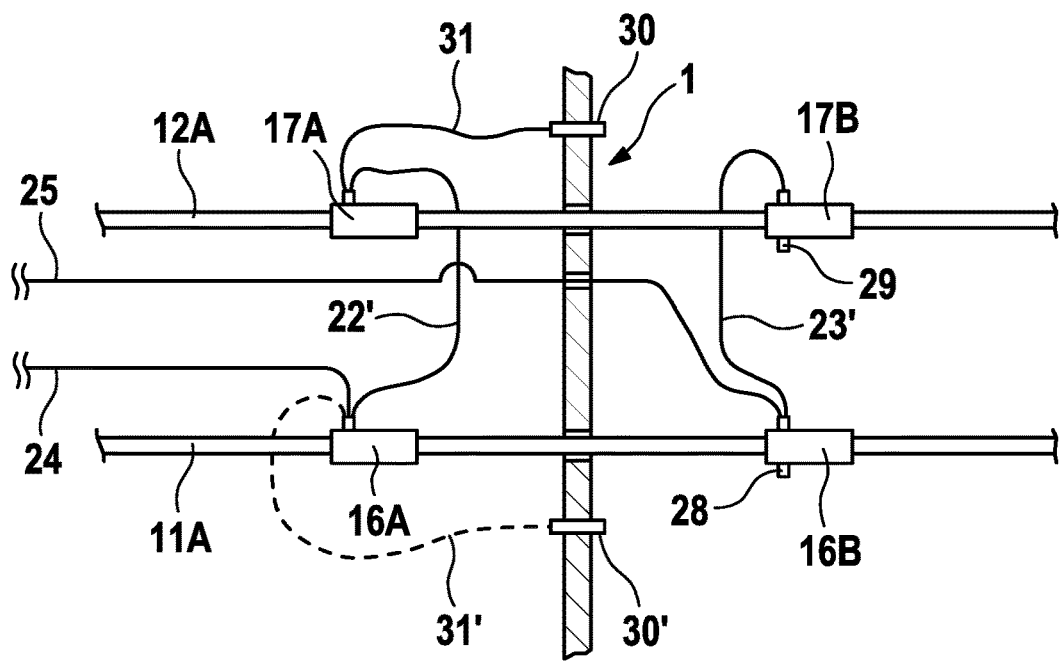
Figure 5:
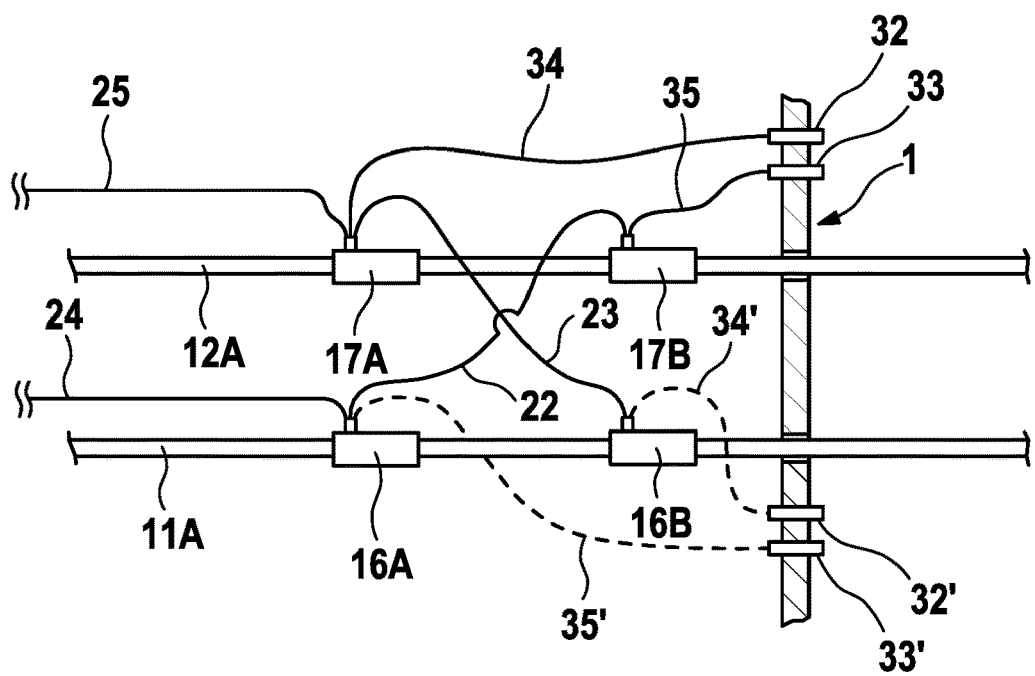
Figure 6:
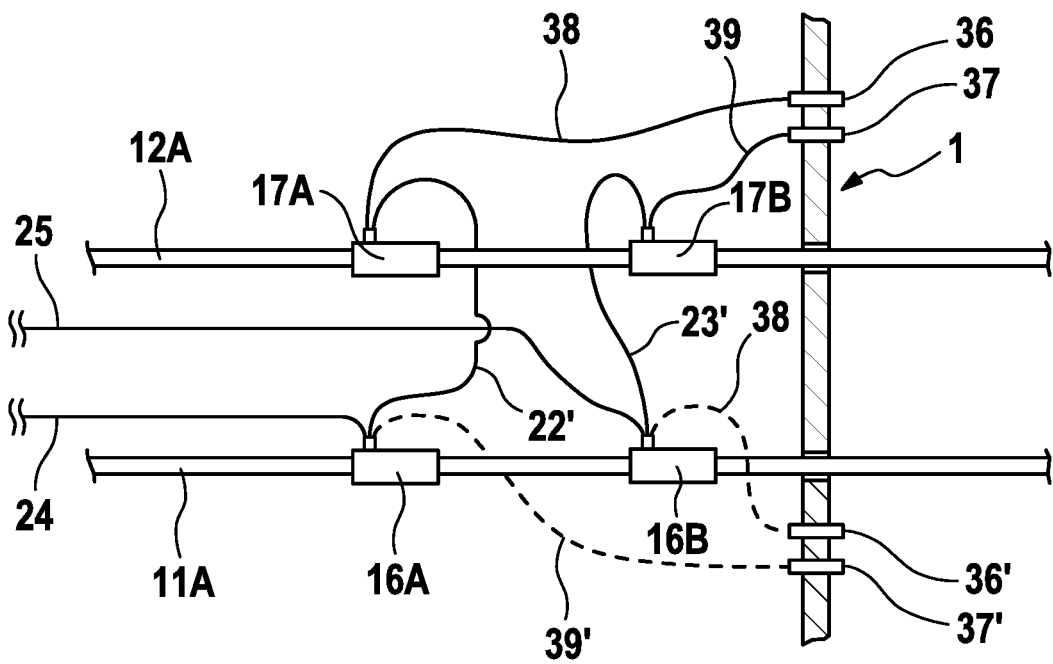
Figure 7:
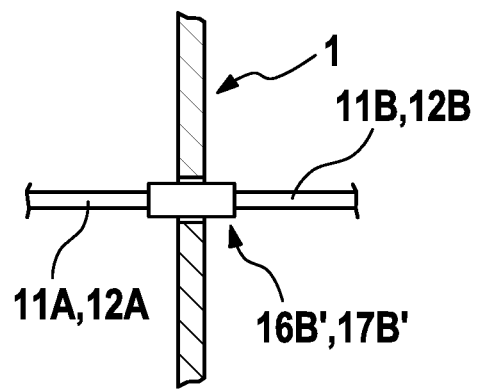

Several embodiments of the invention will be explained in greater detail below with reference to the drawings,
in which:
FIG. 1 is a highly simplified, schematic view of a part of the housing of a dialysis device comprising the circuit arrangement according to the invention,
FIG. 2 is an enlarged view of a protection apparatus for contacting,
FIG. 3 shows a detail of the housing comprising a measurement contact point of an alternative embodiment of the circuit arrangement according to the invention,
FIG. 4 is a schematic view of another embodiment of the circuit arrangement according to the invention,
FIG. 5 shows another embodiment of the circuit arrangement according to the invention, in which all of the protection apparatuses are arranged inside the housing,
FIG. 6 shows another embodiment of the circuit arrangement according to the invention, in which all of the protection apparatuses are arranged inside the housing, and
FIG. 7 is a schematic view of a protection apparatus designed as a housing feedthrough.

FIG. 1 is a highly simplified, schematic view of the components of a blood treatment device as an example of a medical device, which components are essential to the invention. The blood treatment device in the present embodiment is a dialysis device.

The dialysis device comprises a housing 1, which consists of an electrically conductive material (metal housing). The housing 1 may consist of a plurality of housing parts 1A, 1B.

The dialysis device further comprises a dialyser 2, which is only shown schematically in FIG. 1 and is divided into a blood chamber 4 and a dialysate chamber 5 by a semipermeable membrane 3. The dialyser 2 may be attached to a mount 6, which is provided on the outside of the housing 1. A blood supply line 7 leads to the blood chamber 4 of the dialyser 2 and a blood return line 8 leads away from the blood chamber 4. The blood chamber 4 and the blood supply line 7 and blood return line 8 form the extracorporeal blood circuit.

The dialysis device has a dialysate circuit 9 that comprises an apparatus 10 for producing dialysate from fresh water and concentrates. A dialysate supply line 11 leads to an inlet of the dialysate chamber 5 from the apparatus 10 for producing dialysate and a dialysate return line 12 leads to this apparatus 10 or a drain from an outlet of the dialysate chamber 5.

The dialysate supply line 11 and the dialysate return line 12 penetrate the wall of the housing 1 and each have a line portion 11A and 12A, respectively, that is located inside the housing and is referred to in the following as the inner line portion, and a line portion 11B and 12A, respectively, that is located outside the housing and is referred to in the following as the outer line portion.

In addition, the dialysis device comprises a power unit 14 that includes a protective conductor or an equipotential bonding system 15 that can be connected to the protective-conductor system of a fixed electrical installation (not shown) via the protective-earth contact of the mains plug of the dialysis device.

The fluid system of the dialysis device can include additional components, which comprise actuators or sensors, for example.

All of the technical apparatuses of the dialysis device require specific safety measures which are described in the following.

Two protection apparatuses 16A, 16B for electrical contacting are assigned to the dialysate supply line 11 and are designed such that an electrical connection to the fluid in the line 11, in particular to the dialysate flowing to the dialysate chamber 5 of the dialyser 2, can be produced by each protection apparatus. The inner protection apparatus 16A is arranged on the inner line portion 11A, while the other, outer protection apparatus 16B is arranged on the outer line portion 11B. Two protection apparatuses 17A, 17B for electrical contacting are likewise assigned to the dialysate return line 12, in order to produce an electrical connection to the fluid in the line 12, in particular to the dialysate flowing away from the dialysate chamber 5 of the dialyser 2. The inner protection apparatus 17A is again arranged on the inner line portion 12A, while the other, outer protection apparatus 17B is arranged on the outer line portion 12B. The dialysate supply line 11 and return line 12 are flexible hose lines.

FIG. 2 is an enlarged view of one of the protection apparatuses 16A, 16B or 17A, 17B (MOP: means for protection) for electrical contacting. The protection apparatus (MOP) comprises a tubular body 18 made of an electrically conductive material. The protection apparatus can be designed as a metal bush, for example. The two end pieces 19, 20 of the tubular body 18 each comprise a circumferential bead 19A, 20A. The relevant ends of the dialysate supply line 11 and return line 12 are slid onto the end pieces 19, 20 of the tubular body 18. An electrical terminal part 21 is provided on the tubular body 18, which part is used to connect electrical lines in order to produce an electrical connection to the tubular body and to the fluid flowing through the tubular body, in particular the dialysate. Rather than only one terminal part to which a plurality of lines can be connected, a plurality of terminal parts can also be provided on the tubular body, to each of which parts one or more lines can be connected. FIG. 1 shows the connection of the connecting lines to a protection apparatus by means of only one terminal part.

The two inner and outer protection apparatuses 16A, 16B and 17A, 17B of the dialysate supply line 11 and return line 12 are interconnected as follows. The inner protection apparatus 16A or 17A of a fluid line 11 or 12 is electrically connected to the outer protection apparatus 16B or 17B of at least one other fluid line 11 or 12. In the present embodiment, the inner protection apparatus 16A of the dialysate supply line 11 is electrically connected to the outer protection apparatus 17B of the dialysate return line 12 via a connecting line 22, while the inner protection apparatus 17A of the dialysate return line 12 is electrically connected to the outer protection apparatus 16B of the dialysate supply line 11 via a connecting line 23. In addition, the inner protection apparatus 16A of the dialysate supply line 11 is connected to the protective conductor or equipotential bonding system 15 via a connecting line 24, while the inner protection apparatus 17A of the dialysate return line 12 is connected to the protective conductor or equipotential bonding system 15 via a connecting line 25. As a result, each of the protection apparatuses 16A, 16B or 17A, 17B assigned to the individual fluid lines 11, 12 are independently connected to the earth with low resistance. The respective connecting lines 22, 23, 24, 25 are connected to the terminal parts 21 of the protection apparatuses. However, the protection apparatuses 16A, 17A can also have two separate terminal parts for connecting the particular lines 22 and 24 or 23 and 25, respectively.

Earthing of both the dialysate supply line 11 and the dialysate return line 12 is also then ensured if one of the two lines 24 or 25 between the inner protection apparatuses 16A or 17A and the protective conductor or equipotential bonding system 15 is intended to be interrupted.

The protective conductor or equipotential bonding system 15 is connected to the housing 1 via an additional connecting line 26, which housing consists of an electrically conductive material (FIG. 1) in the present example. If the housing 1 does not consist of an electrically conductive material, for example is a plastics housing, the housing comprises a measurement contact point 27 that is accessible from the outside and is connected to the protective conductor or equipotential bonding system 15 via a connecting line 40. FIG. 3 is a schematic view of this measurement contact point 27.

A PE conductor on a metal part, which in this case is a metal bush through which a conductive fluid, in particular dialysate, flows, is considered to be a single protective measure (MOP) within the meaning of the IEC 60601-1 standard. Within the meaning of this standard, the additional separate PE conductor for separate mechanical fastening to said part represents an additional protective measure (MOP) on the same part. The connection of two separate protective conductors is intended above all to improve the electrical safety in particular in the field of hydraulics. An advantage of the safety concept is the simplified safety check (SC).

In the following, a method is described for testing a protective-conductor connection by using the circuit arrangement according to the invention. For the safety check (SC), the resistance between the outer protection apparatus 16B of the dialysate supply line 11 and the housing 1 (FIG. 1) or the measurement contact point 27 of the housing 1 (FIG. 3) is measured by means of a first measurement, and the resistance between the outer protection apparatus 17B of the dialysate return line 12 and the housing 1 or the measurement contact point 27 of the housing 1 is measured by means of a second measurement. In FIG. 1, the separate measurement points on the protection apparatuses are denoted by reference signs 28, 29. The safety check can be carried out using measurement means routinely used in the field. Since all of the measurement means 28, 29 are accessible from the outside, the housing does not need to be opened. A resistance measurement between the measurement points 28, 29 makes it possible to test the connection. If the resistance between the measurement points 28, 29 is high, this indicates that one of the lines 22, 23, 24, 25 is interrupted. Using an additional measurement of the electrical resistance between the measurement points 28 or 29 and the protective-earth contact in the mains plug of the dialysis device, it can be determined whether an adequate connection to the protective-conductor system of the electrical installation can be produced.

FIG. 4 is a schematic view of another embodiment of the circuit arrangement, which differs from the circuit arrangement described with reference to FIGS. 1 to 3 on account of the connection of the individual protection apparatuses. Like parts are provided with the same reference numerals. In the alternative embodiment, the inner protection apparatus 16A of one of the fluid-conducting lines 11A is connected to the inner protection apparatus 17A of the other fluid-conducting line 12A via a connecting line 22', while the outer protection apparatus 16B of one of the fluid-conducting lines 11A is connected to the outer protection apparatus 17B of the other fluid-conducting line 12A via a connecting line 23'. The inner protection apparatuses 16A, 17A are electrically connected to a first star point (not shown in FIG. 4) via a connecting line 24, which star point is connected to the protective conductor, while the outer protection apparatuses 16B, 17B are electrically connected to a second star point (not shown) via a connecting line 25, which second star point is connected to the protective conductor. In this case, too, the fluid-conducting lines are still earthed by means of the redundant star point terminal upon failure of a protective conductor, i.e. when there is an interruption of one of the lines 24, 25 leading to one of the two separate star points connected to the protective conductor. In this embodiment, however, not all of the measurement points are accessible from the outside. The housing 1 therefore has a measurement point 30 which is electrically connected to the inner protection apparatus 17A of one of the fluid-conducting lines 12A via a line 31. In addition, an additional measurement point 30' can be provided, which is electrically connected to the inner protection apparatus 16A of the other fluid-conducting line 11A via a line 31'. The line 31' of the alternative or optional measurement point 30' is shown as a dashed line. The resistance between the two inner protection apparatuses 16A, 17A can be measured from the outside by means of a resistance measurement between the two measurement points 30, 30' and a possible fault can be located. If, for example, the resistance between the two measurement points 30, 30' is low, while the resistance between the measurement point 30 or 30' and the protective conductor (not shown in FIG. 4) is high, it can be concluded that there is a fault in the electrical connection between the inner protection apparatuses 16A, 17A and the protective conductor. A fault in the electrical connection between the inner protection apparatuses 16A, 17A leads to the resistance between a measurement point and the protective conductor being low and the resistance between the other measurement point and the protective conductor being high.

FIG. 5 is a schematic view of another embodiment of the circuit arrangement, which differs from the circuit arrangement described with reference to FIGS. 1 to 3 in that all of the protection apparatuses 16A, 16B and 17A, 17B are arranged inside the housing 1. Like parts are again provided with the same reference signs. In this embodiment, two measurement points 32', 33 are provided on the housing 1, which points are electrically connected to the protection apparatuses 16B, 17B of the two fluid-conducting lines 11A and 12A via lines 34', 35. In addition, two additional measurement points 32', 33 can be provided which are electrically connected to the protection apparatuses 16A and 17A via lines 34', 35. The lines 34, 35' of the optional measurement points 32, 33' are shown. By measuring the resistances between the measurement points 32, 33 and the protective conductor, it can be tested whether the earthing is adequate. If four measurement points 32, 33 and 32', 33' are provided, the electrical resistance between the protection apparatuses 17A and 16B or between the protection apparatuses 16A and 17B can also be measured, and a possible fault can be located without opening the housing.

FIG. 6 is a schematic view of another embodiment of the circuit arrangement, which differs from the circuit arrangement described with reference to FIG. 4 in that all of the protection apparatuses 16A, 16B and 17A, 17B are arranged inside the housing 1. Like parts are again provided with the same reference signs. In this embodiment, two measurement points 36, 37 are provided on the housing 1, which points are electrically connected to the protection apparatuses 17A, 17B of one of the two fluid-conducting lines 12A via lines 38, 39. In addition, two additional measurement points 36', 37' can be provided which are electrically connected to the protection apparatuses 16A, 16B of the other fluid-conducting line 11A via lines 38', 39'. The lines 38', 39' of the alternative or optional measurement points 36', 37' are shown as a dashed line. The earthing can be tested, again by means of the above-described resistance measurements, using the measurement points that are directed outwards.

FIG. 7 is a highly simplified schematic view of a protection apparatus which is designed as a housing feedthrough. Said protection apparatus 16B', 17B' can be one of the two protection apparatuses 16B or 17B, which are shown in FIGS. 1 to 6. In this embodiment, the housing 1 can consist of an electrically conductive material. If the protection apparatus comprises a body made of an electrically conductive material, through which the fluid flows, said body is preferably electrically insulated with respect to the electrically conductive housing.

In the above-described embodiments, the individual measurement points can be designed in the same way as the measurement contact point described with reference to FIG. 3.

The concept according to the invention can also be used for inlets and outlets or interfaces of the extracorporeal blood circuit.

The invention claimed is:

1. Circuit arrangement for a protective-conductor connection to at least two fluid-conducting lines the circuit arrangement comprising a plurality of protection apparatuses for electrical contacting which are designed such that an electrical connection to a fluid in the line can be produced using each protection apparatus for electrical contacting,
wherein
at least two protection apparatuses for electrical contacting are assigned to each fluid-conducting line, and
the at least two protection apparatuses for electrically contacting a fluid-conducting line are each electrically connected to another protection apparatus for electrically contacting another fluid-conducting line.

2. Circuit arrangement according to claim 1, wherein, out of the at least two protection apparatuses for electrical contacting assigned to each fluid-conducting line, at least one protection apparatus for electrical contacting is assigned to a line portion of the fluid-conducting line that is inside the housing and at least one protection apparatus for electrical contacting is assigned to a line portion of the fluid-conducting line that is outside the housing, at least in part.

3. Circuit arrangement according to claim 2, wherein a protection apparatus for electrically contacting a fluid-conducting line that is assigned to the line portion of one of the fluid-conducting lines that is inside the housing is electrically connected to a protection apparatus for electrically contacting another fluid-conducting line that is assigned to the line portion of the other fluid-conducting line that is outside the housing, at least in part.

4. Circuit arrangement according to claim 3, wherein the protection apparatuses assigned to the line portion of the fluid-conducting line that is inside the housing are each connected to a protective conductor or an equipotential bonding system by means of an electrical connecting line.

5. Medico-technical device comprising a housing and at least two fluid-conducting lines, wherein the medico-technical device is a circuit arrangement according to claim 1.

6. Medico-technical device according to claim 5, wherein the at least two fluid-conducting lines are guided outwards from the interior of the housing.

7. Medico-technical device according to claim 5, wherein the at least two fluid-conducting lines are part of a fluid system of the medico-technical device.

8. Medico-technical device according to claim 5, wherein a medical fluid is located in the at least two fluid-conducting lines.

9. Medico-technical device according to claim 5, wherein the medico-technical device comprises a first fluid-conducting line and a second fluid-conducting line, the two fluid-conducting lines forming a fluid circuit.

10. Medico-technical device according to claim 5, wherein the medico-technical device is a blood treatment device.

11. Circuit arrangement according to claim 1, wherein at least one protection apparatus is designed as a housing feedthrough.

12. Circuit arrangement according to claim 11, wherein the at least one protection apparatus designed as a housing feedthrough is electrically insulated with respect to a housing made of an electrically conductive material.

13. Medico-technical device comprising a housing and at least two fluid-conducting lines, wherein the medico-technical device is a circuit arrangement according to claim 4.

14. Medico-technical device according to claim 13, wherein the housing consists of an electrically conductive material, the housing being electrically connected to the protective conductor or equipotential bonding system.

15. Medico-technical device according to claim 13, wherein the housing consists of an electrically non-conductive material, an electrical measurement contact point on the housing being electrically connected to the protective conductor or equipotential bonding system, which point is accessible from the outside.

16. Medico-technical device according to claim 13, wherein the protective conductor or equipotential bonding system is connected to the protective conductor system of a fixed electrical installation.

17. Method for testing a protective-conductor connection to at least two fluid-conducting lines that are guided outwards from the interior of a housing of a medico-technical device by means of a circuit arrangement according to claim 4, wherein the electrical resistance between the protection apparatuses for electrical contacting that are assigned to the line portions of the fluid-conducting lines that are outside the housing, at least in part, and the protective conductor or equipotential bonding system is measured.

18. Method according to claim 17, wherein the protective conductor or equipotential bonding system is electrically connected to a housing made of an electrically conductive material, the electrical resistance between the protection apparatuses for electrical contacting that are assigned to the line portions of the fluid-conducting lines that are outside the housing, at least in part, and the housing being measured.

19. Method according to claim 17, wherein the protective conductor or equipotential bonding system is electrically connected to an electrical measurement contact point, which is accessible from the outside, on a housing made of an electrically non-conductive material, the electrical resistance between the protection apparatuses for electrical contacting that are assigned to the line portions of the fluid-conducting lines that are outside the housing, at least in part, and the measurement contact point being measured.

* * * * *